United States Patent [19]

De Matteis

[11] Patent Number: 4,604,350
[45] Date of Patent: Aug. 5, 1986

[54] SCREENING TEST FOR BETA-THALASSEMIA TRAIT AND A DIAGNOSTIC KIT FOR ITS INDIVIDUALIZATION

[76] Inventor: Maria C. De Matteis, Piazza Isotta Nogarola, 15 - 37131 Verona, Italy

[21] Appl. No.: 485,327

[22] Filed: Apr. 15, 1983

[30] Foreign Application Priority Data

Apr. 29, 1982 [IT] Italy .............................. 41564 A/82

[51] Int. Cl.$^4$ ....................... C12Q 1/06; G01N 33/72
[52] U.S. Cl. ........................................ 435/29; 436/66
[58] Field of Search .................... 435/2, 3, 4, 6, 7, 34, 435/29, 240, 241, 260, 289, 300, 301, 808, 810, 287, 291, 293, 296; 436/66, 63, 161, 149, 501, 164, 165, 805, 809, 811, 826; 422/72, 55; 356/39, 441, 442, 42, 243, 246, 432–434, 244

[56] References Cited

U.S. PATENT DOCUMENTS

| | | | |
|---|---|---|---|
| 3,617,222 | 11/1971 | Matte | 422/73 |
| 4,010,078 | 3/1977 | Taylor | 435/301 |
| 4,012,288 | 3/1977 | Lyman et al. | 435/301 |
| 4,038,149 | 7/1977 | Liner et al. | 435/300 |
| 4,154,795 | 5/1979 | Thorne | 435/300 |
| 4,159,895 | 7/1979 | Shine | 422/73 |
| 4,284,725 | 8/1981 | Fennel, III et al. | 435/301 |
| 4,292,273 | 9/1981 | Butz et al. | 435/301 |
| 4,353,988 | 10/1982 | Couse et al. | 435/297 |

OTHER PUBLICATIONS

De Gier, J. et al, Experientia, vol. 22, pp. 20–21 (1966).
Wessels, J. M. C. et al, Biochim. Biophys. Acta, vol. 291, pp. 178–189; 190–196 (1973).
Jacobs, M. H. et al, J. Experimental Zoology, vol. 113, pp. 277–300 (1950).
Kroes, J. et al, Biochim. Biophys. Acta, vol. 249, pp. 647–650 (1971).
Moore, T. J., J. Lipid Research, vol. 9, pp. 642–646 (1968).
De Gier, J. et al, Biochim. Biophys. Acta, vol. 49, pp. 286–296.
Gottfried, E. L. et al, Jour. Lab. Clin. Med., vol. 84, No. 5 (1974), pp. 746–751, "Glycerol Lysis Time of Incubated Erythrocytes in the Diagnosis of Hereditary Spherocytosis".
Gottfried, E. L. et al, Jour. Lab. Clin. Med., vol. 83, No. 2 (1974), pp. 323–333, "Glycerol Lysis Time as a Screening Test for Erythrocyte Disorders".
Chemical Abstracts, vol. 91, 1979, Abstract No. 37163k (1979), Zanella, A. et al, "Membrane Abnormalities of Pyruvate Kinase Deficient Red Cells".

Primary Examiner—Thomas G. Wiseman
Assistant Examiner—M. Moskowitz
Attorney, Agent, or Firm—Bucknam and Archer

[57] ABSTRACT

A screening test for beta-thalassemia trait carriers is carried out by mixing 10 μl of blood of the patient with 2 ml of an aqueous solution prepared from glycerol, sodium chloride, sodium dihydrogen phosphate, disodium hydrogen phosphate, sodium azide, Acid Green 5 to obtain a suspension. A well cluster, having several wells is used. The suspension is formed in one well and the turbidity is determined by placing a reading scale under the cluster.

3 Claims, 1 Drawing Figure

U.S. Patent      Aug. 5, 1986      4,604,350
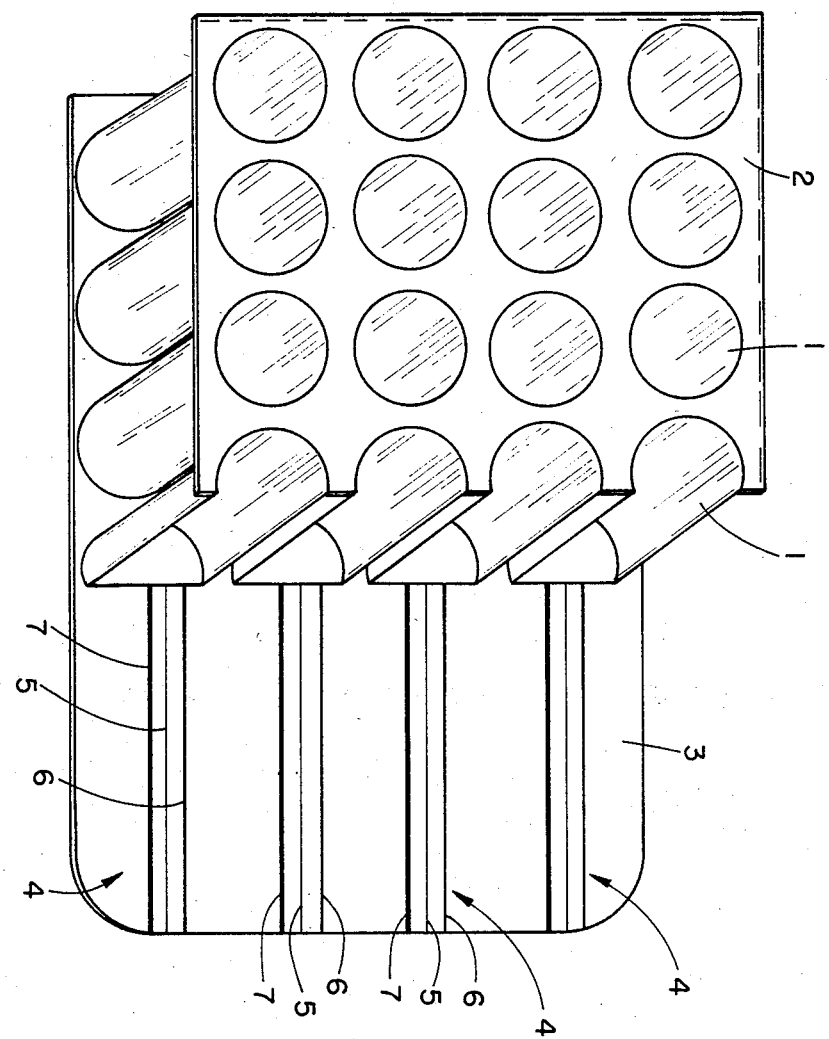

SCREENING TEST FOR BETA-THALASSEMIA TRAIT AND A DIAGNOSTIC KIT FOR ITS INDIVIDUALIZATION

Hemolysis of the erythrocytes by glycerol has been studied by many authors, among whom: M. H. Jacobs, et al, J. Exper. Zool. 113, 272, (1950); J. Kroes, et al, Biochim. Biophys. Acta 249, 647, (1971); T. J. Moore, J. Lipid Res. 9, 642 (1968); J. De Gier, et al, Biochim. Biophis, Acta 49, 286 (1961) and Experientia 22, 20 (1966); J. M. C. Wessels, et al, Biochim. Biophys. Acta 291, 178–196 (1973). E. L. Gottfried and N. A. Robertson, Blood 40, 940 (1972), J. Lab. Clin. Med. 83, 323–333 (1974) and 84, 746–751, describe methods for screening erythrocyte abnormalities like the thalassemia trait carriers, iron deficiency anemia, hereditary spherocytosis, sickle-cell anemia, based on the lysis time of the erythrocytes suspended in a 0.3M aqueous buffered solution of glycerol (glycerol lysis test, GLT).

The present invention is based on a similar principle bar is far more reliable and simpler. A. Zanella et al, British Journal of Haematology, 45, 481–6 (1980), describes a modification of GLT, named Acidified Glycerol Lysis Test (AGLT) as a screening test for hereditary spherocytosis.

The object of the present invention is to provide a screening test for beta-thalassemia trait carriers with a diagnostic kit for its diagnosis.

The thalassemia syndromes are a group of inherited anemias in man, which are transferred as semi-dominant autosomal conditions. There are a number of thalassemias, the main and most frequent of which are named "alpha", "beta" and "delta-beta".

The "beta" and "delta-beta" forms involve a diminished synthesis of the beta-hemoglobin chains and assume a great importance from a pathological point of view. In fact, the hereditary transmission of the beta-thalassemia trait carriers in the heterozygous state, i.e. from only one of the parents to 50% of the children, according to the Mendelian Laws, produces only slight hematological abnormalities in the children (similar to those of the carrier parent), without any symptoms of the disease (beta-thalassemia minima).

This fact leads to the diffusion of the beta-thalassemia trait carriers among the population without any evident damage. On the contrary, the contemporaneous transmission of the carriers from both parents having microcythemia causes in 25% of the children severe anemia, Cooley anemia, which appears a few months after birth and which seriously compromises the life of the patients, most of whom die young.

At present the thalassemia syndromes are considered as social diseases due to the considerable diffusion of the beta-thalassemia trait carriers mainly in the Mediterranean area and now also in other parts of the world due to emigration. Notwithstanding the improvements in medicine up to the present time, Cooley anemia has been incurable and therefore, it must be prevented. At present the preventive measures consists of:

(a) health education and eugenics intended to inform the population mainly in the areas in which the risk is greatest;

(b) pre-matrimonial diagnosis of the beta-thalassemia trait carriers;

(c) prenatal diagnosis of the risk in pregnancy.

At present the first two methods have greater probabilities of success than in the past because of the improvement in the cultural, social and economical standards of the population and because of the ample availability of effective contraceptive means.

Therefore, simple, efficient and widely utilizable diagnostic means are necessary.

At present several different screening tests are being used and it is always necessary to combine several tests in order to increase the sensitivity of the diagnosis, as, till now, there does not exist a diagnostic test which combines all optimal characteristics.

An object of the present invention is to provide a diagnostic method which overcomes the drawbacks of the tests used up to the present.

Another object is to provide a diagnostic method which may be carried out in a short time for a number of people with great ease.

Still another object is to provide a diagnostic kit of high sensitivity, which enables the detection of all people carrying the beta-thalassemia trait, without any false negative result. Another object is to provide a method for the detection of beta-thalassemia carriers which is economical.

The invention will be described hereinbelow by reference to the drawing, FIG. 1 which illustrates the apparatus for carrying out the method of the invention.

The apparatus consists of a plurality of cylindrical wells, having a transparent bottom, which is called the "wells cluster". The wells are designated by numeral 1 and are located in plate 2. The scale is designated by numeral 3 and consists of parallel lines 4. The method according to the present invention involves the following steps:

(a) preparing solution A from 13.70 grams of glycerol, 3.40 grams of sodium chloride, 1.00 gram of sodium dihydrogen phosphate, 0.44 grams of disodium hydrogen phosphate, 0.10 grams of sodium azide, 0.03 grams of Acid Green 5 and bidistilled water to make a final volume of 1 liter; Acid Green 5 also called Green Light is a dye of empirical formula $C_{37}H_{34}N_2Na_2O_9S_3$;

(b) placing 2 cc of the solution prepared in step (a) in one well of the well cluster;

(c) mixing 10 μl of venous or capillary blood, drawn from the subject with the sample of the solution placed in the well in step (b);

(d) waiting 30–45 minutes and then gently stirring;

(e) placing the cluster on the reading scale and determining the turbidity on the basis of the number and the type of the more or less visible lines of the scale. This scale 3 consists of a thin card which has some groups of parallel lines arranged in such a way as to be located under the median zone of the wells of the cluster, the lines being of different thickness so as to be more or less visible according to the turbidity of the suspension.

The analysis may be carried out by means of a spectrophotometer, by suitably utilizing the same solution, by comparing a test suspension with a suspension used for comparison.

The invention is better illustrated by means of the following detailed description of preferred forms of execution which, however, must in no way be construed as a limitation of the scope of the invention itself.

According to the present invention, solution A is prepared as follows:

| Reagent | Grams/liter of H$_2$O | mmoles/liter of H$_2$O |
|---|---|---|
| Glycerol | 13.70 | 148.5 |

| Reagent | Grams/liter of H$_2$O | mmoles/liter of H$_2$O |
|---|---|---|
| Sodium chloride | 3.40 | 58.0 |
| Sodium dihydrogen phosphate | 1.00 | 7.0 |
| Disodium monohydrogen phosphate | 0.44 | 3.0 |
| Sodium azide | 0.10 | 1.5 |
| Acid Green 5 | 0.03 | |
| Bidistilled water to a total final volume of 1000 ml | | |
| pH = 6.5 | | |
| mOs M/Kg = 285 | | |

The groups of lines in the reading scale are shown in the figure, made up of a median thin line (5), a thicker upper line (6) and an even larger lower line (7).

For a semi-quantitative analysis, a specimen of blood is drawn from the subject to be examined and 10 µl of capillary or venous blood (in the latter case drawn with an anticoagulant like EDTA or heparin) measured by means of a glass micropipette are added to 2 ml of the solution previously put in a well of the wells cluster. The blood has to be freshly drawn, or kept at +4° C. for not longer than 4-6 hours. After 30-45 minutes at room temperature, the suspension is gently stirred by means of the micropipette. After superimposing the tissue culture cluster on the reading scale, the degree of turbidity is determined on the basis of the degree of clarity of the different sized lines of the reading scale observed through the transparent bottom of the wells.

The results are expressed as follows:

negative = the three lines appear clear and distinct. The subject is clearly not affected by beta-thalassemia trait;

intermediate = only the largest lines are visible, but not clearly. This may be a suspect carrier of beta-thalassemia trait, or, sometimes a subject affected by another pathological condition mainly other types of thalassemia or iron deficiency anemia, that is to say a "false positive" for the beta-thalassemia trait;

positive = the lines of the reading scale are not clearly distinguishable. The subject is a carrier of beta-thalassemia trait.

The different turbidity comes from the fact that mixing minimal amounts of blood with the solution causes the hemolysis of normal red cells in a few minutes, while the red cells of the carriers of beta-thalassemia trait do not hemolyze. Therefore, the phenomenon can be visually evaluated based on the degree of turbidity of the suspension made in the above described proportions of the solution and of the blood to be tested.

A quantitative evaluation of the degree of turbidity can also be carried out. The following solution designated herein as solution B is used in addition to the solution described hereinabove, which is designated as solution A. Solution B consists of:

| Reagents | Grams/liter of H$_2$O | mmoles/liter of H$_2$O |
|---|---|---|
| Sodium Chloride | 9.00 | 150 |
| Acid Green 5 | 0.03 | 0.04 |

This solution is also called the "100% turbidity" solution.

A portion of 5 µl of capillary or uncoagulated venous blood are carefully suspended in 3 ml of the solution A prepared for the semiquantitative analysis, which therefore becomes a test suspension, while 5 µl of the same blood are suspended in 3 cc of the comparison 100% turbidity solution, solution B. The suspension is the comparison suspension After 30-45 minutes at room temperature the suspensions are gently and carefully mixed by turning upside down and the turbidity is spectrophotometrically determined as optical density (O.D.) of both the suspensions at 495 nm wavelength, by using as "blank" the solution A without any blood added.

The degree of turbidity is calculated as follows:

$$\text{turbidity } \% = \frac{O.D. \text{ test suspension}}{O.D. \text{ comparison suspension}} \times 100$$

The results are so interpreted:
negative = turbidity less than 30%
intermediate = turbidity between 30% and 50%
positive = turbidity more than 50%

The diagnostic procedure according to the present invention is comparable to an osmotic fragility test "in a test tube" which uses an hypotonic saline solution containing 0.375% of sodium chloride in weight, in order to characterize the subjects having a diminished osmotic fragility of the erythrocytes, most of whom are affected by thalassemia trait.

However, this test results positive in about the 95% of the beta-thalassemia carriers, that is to say that there is about 5% "false negative"; this percentage is not irrelevant from a diagnostic point of view in the screening tests, because it involves the failure in a number of carriers.

The diagnostic procedure according to the present invention distinguishes itself from the osmotic fragility test "in a test tube" both for its greater sensitivity and because it is not a simple test of osmotic fragility.

In fact the turbidimetric test is based on the following principle:

the intracellular penetration of the glycerol is very fast and quantitatively high in the normal erythrocytes and drags with it some water causing their swelling over the critical volume of lysis, hence hemolysis and clarification of the suspension. On the contrary, the thalassemic erythrocytes have an increased ratio surface/volume and hence they need a greater amount of water to reach the critical volume of lysis; moreover, the intrinsic distinctive features of the structure of their membrane makes them less permeable to the glycerol. For these reasons, only a low percent of the thalassemic erythrocytes hemolyze by means of the solution used in the procedure and the amount of "resistant" erythrocytes lasts unchanged, thus keeping the suspension turbid.

This fact allows the semi-quantitative or quantitative determination of the result also many hours after the suspension has been prepared. In other words, the extent of the hemolysis does not depend on the time but only on the percentage of cells which naturally "resist" the glycerol penetration and consequently the related phenomena. The high sensitivity and specificity of the test and its remarkable rapidity and ease of completion result from the above mentioned phenomena. All these properties and pecularities make the procedure of the present invention far better, both from a methodological point of view and for the results, than existing tests like the glycerol lysis test (GLT) described by E. L. Gottfried and N. A. Robertson (Journal Laboratory and Clinical Medicine 83 (1974) pp. 323-333), which is more complex and less sensitive even though it is based on an analogous principle.

The procedure according to the present invention is particularly suitable for mass screenings and therefore, for a high number of specimens in the detection of the thalassemia trait. At the same time, mainly when used for quantitative screening, it is particularly suitable in a laboratory of clinical chemistry instead of the present tests based on the osmotic fragility of the erythrocytes which are more complicated and/or less precise and reliable.

I claim:

1. A method for detecting quantitatively beta-thalassemia in a patient which consists of:
   (a) preparing an aqueous solution A containing 148.5 mmoles of glycerol, 58 mmoles of sodium chloride, 7 mmoles of sodium dihydrogen phosphate, 3 mmoles of disodium monohydrogen phoshate, 1 mmole of sodium azide, 0.04 mmoles of Acid Green 5 ($C_{37}H_{34}N_2Na_2O_3S_9$) of pH 6.5 per liter of solution;
   (b) placing 3 cc of said solution A from step (a) in a test tube;
   (c) adding to said solution A 5 microliters of capillary freshly drawn blood or venous blood collected in the presence of an anticoagulant, stirring therewith to obtain a suspension and incubating said suspension for 30–45 minutes at room temperature to obtain the test suspension;
   (d) preparing solution B from 150 mmoles of sodium chloride and 0.04 mmoles of Acid Green 5, said solution B being the 100% turbidity solution;
   (e) placing 3 ml of said solution B from step (d) in a second test tube;
   (f) preparing a blood suspension having 100% turbidity by shaking said solution B with 5 microliters of the blood from the same patient to obtain the comparison suspension;
   (g) separately measuring at 495 nm wavelength the optical densities of said carefully stirred blood suspensions from steps (c) and (f) against said solution A from step (a) without blood added, and using said solution A as a blank;
   (h) comparing the degree of turbidity based on values calculated as percent turbidity according to the equation $$\frac{O.D. \text{ test suspension from step } (c)}{O.D. \text{ comparison suspension from step } (f)} \times 100. = \% \text{ turbidity}$$

and when the turbidity value is lower than 30%, said patient is normal, when the turbidity is between 30 and 50%, said patient is suspect and when the turbidity value is greater than 50%, said patient is a carrier of beta-thalassemia trait.

2. A method for carrying out a test to detect beta-thalassemia in a patient, which consists of:
   (a) preparing an aqueous solution A containing 148.5 mmoles of glycerol, 58 mmoles of sodium chloride, 7 mmoles of sodium dihydrogen phosphate, 3 mmoles of disodium monohydrogen phosphate, 1.5 mmole of sodium azide, 0.04 mmole of Acid Green 5 ($C_{37}H_{34}N_2Na_2O_3S_9$) of pH 6.5 per liter of solution;
   (b) placing 2 cc of the solution A from step (a) in one well of a well cluster of a plurality of cylindrical wells, having transparent bottom;
   (c) adding to said solution A in said well 10 microliters of capillary freshly drawn blood or venous blood collected in the presence of an anticoagulant, stirring therewith to obtain a suspension and incubating said suspension for 30–45 minutes at room temperature;
   (d) juxtaposing the wells cluster to a grid consisting of a thin card having groups of three parallel lines of different thickness so that each group of three lines cross the median bottom zone of said well; and
   (e) measuring after gentle stirring the degree of turbidity of said suspension by the degree of visibility of said grid lines, so that said test is considered negative when all three grid lines are clearly visible, said test is slightly positive indicative of a suspect patient when only the larger grid lines are faintly visible, and said test is positive when all three grid lines are not visible.

3. A kit for screening a patient for beta-thalassemia which comprises (a) a cluster of a plurality of cylindrical wells (1) having a flat transparent bottom, said wells being located in a plate (2); (b) a grid (3) consisting of a card imprinted with four groups of three parallel lines each, the median line being thin, the upper line being thicker and the lower line being still thicker, said grid being located under the median zone of the wells of the cluster and (c) a container containing an aqueous solution A containing 148.5 mmoles of glycerol, 58 mmoles of sodium chloride, 7 mmoles of sodium dihydrogen phosphate, 3 mmoles of disodium monohydrogen phosphate, 1.5 mmole of sodium azide, 0.04 mmole of Acid Green 5 ($C_{37}H_{34}N_2Na_2O_3S_9$) of pH 6.5 per liter of solution wherein the components of said kit are present in amounts sufficienty to detect beta-thalassemia.

* * * * *